(12) United States Patent
Lalvani

(10) Patent No.: US 8,105,797 B2
(45) Date of Patent: Jan. 31, 2012

(54) DIAGNOSTIC TEST

(75) Inventor: Ajit Lalvani, Oxford (GB)

(73) Assignee: Ajit Lalvani, Oxford (GB)

( * ) Notice: Subject to any disclaimer, the term of this patent is extended or adjusted under 35 U.S.C. 154(b) by 648 days.

(21) Appl. No.: 10/593,384

(22) PCT Filed: Mar. 21, 2005

(86) PCT No.: PCT/GB2005/001062
§ 371 (c)(1),
(2), (4) Date: Aug. 29, 2008

(87) PCT Pub. No.: WO2005/090988
PCT Pub. Date: Sep. 29, 2005

(65) Prior Publication Data
US 2008/0305503 A1  Dec. 11, 2008

(30) Foreign Application Priority Data
Mar. 19, 2004 (GB) .................................. 0406271.7

(51) Int. Cl.
*G01N 33/00* (2006.01)
*A61K 39/04* (2006.01)
*A61K 39/00* (2006.01)

(52) U.S. Cl. ...... 435/7.24; 424/9.1; 424/9.2; 424/184.1; 424/185.1; 424/234.1; 424/248.1

(58) Field of Classification Search .................... 424/9.1, 424/9.2, 184.1, 185.1, 234.1, 248.1; 435/7.24
See application file for complete search history.

(56) References Cited

FOREIGN PATENT DOCUMENTS

| EP | 1 350 839 A1 | 10/2003 |
|---|---|---|
| WO | WO 00/26248 A2 | 5/2000 |
| WO | WO01/79274 | * 10/2001 |
| WO | WO 01/79274 A2 | 10/2001 |
| WO | WO 02/054072 | 7/2002 |
| WO | WO 03/070981 A2 | 8/2003 |
| WO | WO 03/093307 A2 | 11/2003 |

OTHER PUBLICATIONS

Liu, X, et al., "Evaluation of T-Cell Responses to Novel RD1—and RD2—Encoded Mycobacterium tuberculosis Gene Products for Specific Detection of Human Tuberculosis Infection," Infection and Immunity, vol. 72, No. 5, May 2004, pp. 2574-2581.

International Search Report and the Written Opinion of he International Searching Authority, issued for PCT/GB2005/001062, on Nov. 8, 2005.

* cited by examiner

*Primary Examiner* — Rodney P. Swartz
(74) *Attorney, Agent, or Firm* — Fulbright & Jaworski L.L.P.

(57) ABSTRACT

The invention provides a method of diagnosing *Mycobacterium tuberculosis* infection in a human, or of determining whether a human has been exposed to *Mycobacterium tuberculosis*, comprising: (i) contacting T-cells from said human with one or more of (a) a peptide having the sequence shown in SEQ ID NO: 1; (b) a peptide having or comprising the sequence of at least 8 consecutive amino acids of the sequence shown in SEQ ID NO: 1; or (c) a peptide having or comprising a sequence which is capable of binding to a T-cell receptor which recognizes a peptide as defined in (a) or (b); and (ii) determining whether any of the said T-cells recognize said peptide, wherein steps (i) and (ii) are optionally carried out in vitro.

19 Claims, 5 Drawing Sheets

```
                Peptide 119-133      Peptide 139-153
      +      +++          +  +++++++  ++      ++  +++          +
100 MATTPSLPEIAANHITQAVLTATNFFGINTIPIALTEMDVFIRMWNQAALAMEVYQAETAV 160  Rv3873
    -AMVPP-PVVAANRAQHMSLVATNFFGQNTPAIAATEAQYE-EMWAQDAAAMYGY------        PPE Motif
```

FIG. 3

DIAGNOSTIC TEST

FIELD OF THE INVENTION

The invention relates to a method of diagnosis of *Mycobacterium tuberculosis* infection in a human. It also relates to peptide compositions and a kit which can be used to carry out the diagnostic method.

BACKGROUND TO THE INVENTION

Accurate diagnosis of tuberculosis infection is essential for the treatment, prevention and control of this resurgent disease. Since *Mycobacterium tuberculosis* (MTB) is often difficult to culture from patients with active TB, and impossible to culture from healthy latently infected people, an immune-based diagnostic test indicating the presence or absence of MTB infection would be very useful for diagnosis of active TB and screening for latent MTB infection.

The only widely used test is the century-old tuberculin skin test (TST) or Mantoux test which is based on the detection of a delayed type hypersensitivity (DTH) response to an intradermal administration of a Purified Protein Derivative of the mycobacterium. This test has many drawbacks foremost amongst these is its poor specificity which results from the broad antigenic cross-reactivity of purified protein derivative (PPD), a crude mixture of over two hundred MTh proteins widely shared between MTh, *M. bovis* Bacillus Calmette-Guerin (BCG) and most environmental mycobacterial. Hence, false-positive results are common in people with environmental mycobacterial exposure and previous BCG vaccination. This presents a significant problem because most of the world's population is BCG-vaccinated and the confounding effect of BCG persists for up to 15 years after vaccination.

Comparative genomics has identified several genetic regions in MTB and *M. bovis* that are deleted in *M. bovis* BCG. Several regions of difference, designated RD1-RD16, between MTB or *M. bovis* and BCG have been identified. All represent parts of the *M. bovis* genome deleted during prolonged in vitro culture. RD-1 was deleted before 1921, when BCG was first disseminated internationally for use as a vaccine. RD-1 is thus absent from all vaccine strains of BCG, as well as most environmental mycobacteria, but is still present in the *Mycobacterium tuberculosis* complex, including all clinical isolates of MTB and *M. bovis*. There are nine open reading frames (ORFs) in the RD1 gene region. Early secretory antigen target-6 (ESAT-6) and culture filtrate protein 10 (CFP10) are encoded in RD-1 and have been intensively investigated in animal models and humans over the last few years. ESAT-6 and CPF10 are strong targets of the cellular immune response in animal models, tuberculosis patients and contacts and so may be used in new specific T cell-based blood tests which do not cross-react with BCG.

Cellular immune responses to gene products from RD1, RD2 and RD14 have recently been investigated in *M bovis*-infected and BCG-vaccinated cattle. Eight antigens were deemed to be potent T cell antigens, Rv1983, Rv1986, Rv3872, Rv3873, Rv3878, Rv3879c, Rv1979c, and Rv1769) (Cockle et al., 2002, Infect. Immun. 70:6996-7003). However it is not possible to predict based on the antigens which are T-cell antigens in cattle which will be T-cell antigens in humans. As well as other differences in antigen processing, presentation and recognition, cattle have different MHC molecules from humans, and thus are expected to recognise different antigens.

SUMMARY OF THE INVENTION

The present inventors have identified Rv3879c as a major T-cell antigen in humans, with 45% of tuberculosis patients responding to peptides from the Rv3879 gene product. Only one of 38 (2.6%) BCG-vaccinated donors responded to peptides from Rv3879c. The high specificity of Rv3879c peptides, together with their moderate sensitivity in tuberculosis patients, identify these peptides as candidates for inclusion in new T cell-based tests for MTB infection.

Crucially, the inventors identified 3 individuals (out of 49 culture confirmed TB patients) who responded to Rv3879c peptides and who did not respond to any of 35 overlapping 15mer peptides spanning the length of ESAT-6 and CFP10 (which are known to be immunodominant MTB antigens of diagnostic utility). This result shows that Rv3879c peptides can be used to increase the sensitivity of diagnostic tests which use ESAT-6 and CFP10 peptides. This increase in sensitivity (which was 6% in the present study of 49 TB patients) is clinically very important. A very high sensitivity allows doctors to rule out the possibility of tuberculosis when a diagnostic test is negative. In particular immune based diagnostic tests (including the in vivo skin test) may give false negative results in immunosuppressed individuals because of their limited sensitivity. A higher diagnostic sensitivity will allow doctors to accurately detect TB infection even in these vulnerable immunosuppressed patients who are at the highest risk of severe and disseminated tuberculosis.

Accordingly, the invention provides a method of diagnosing *Mycobacterium tuberculosis* infection in a human, or of determining whether a human has been exposed to *Mycobacterium tuberculosis*, comprising:

(i) contacting T-cells from said human with one or more of
   (a) a peptide having the sequence shown in SEQ ID NO: 1;
   (b) a peptide having or comprising the sequence of at least 8 consecutive amino acids of the sequence shown in SEQ ID NO: 1; or
   (c) a peptide having or comprising a sequence which is capable of binding to a T-cell receptor which recognises a peptide as defined in (a) or (b); and (ii) determining whether any of the said T-cells recognise said peptide.

Figure 1A:
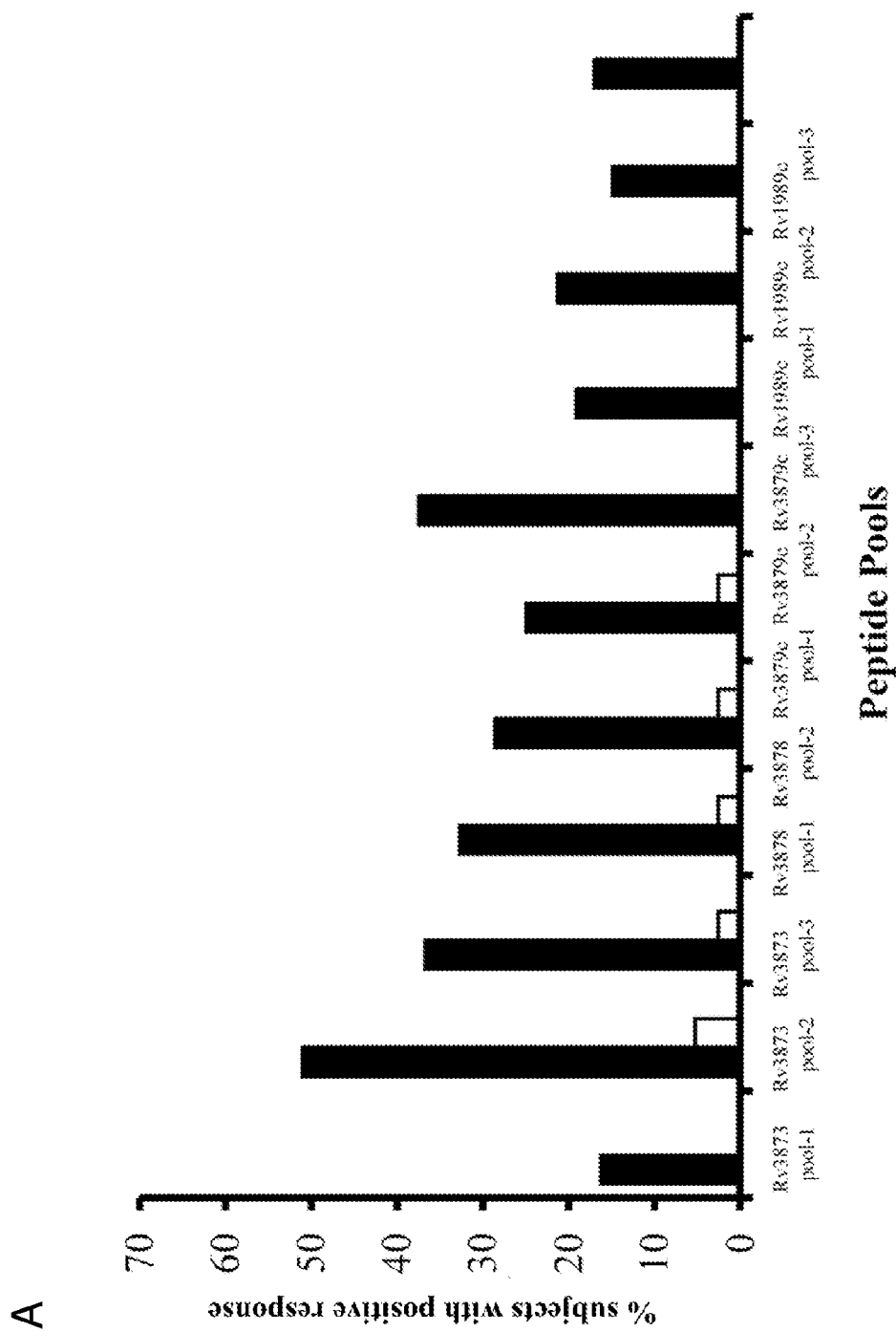
FIG. 1 shows the proportion of culture-confirmed TB patients (n=49) and healthy, unexposed BCG vaccines (n=38) responding in IFN-γ-ELISPOT to peptide pools from the four RD region gene products. PBMCs from each participant were tested using the IFN-γ-ELISPOT assay with peptide pools of between 5 and 7 peptides representing different antigens from RD1 (Rv 3873, Rv3878, Rv3879c) and RD2 (Rv1989c).

A: Percentage of culture confirmed TB patients and unexposed BCG vaccinees who responded to each peptide pool in IFN-γ-ELISPOT.

B: Percentage of culture confirmed TB patients and unexposed BCG vaccinees who responded to one or more peptide pools from each of the RD1 and RD2 gene products. The right hand-most column shows the percentage of donors who responded to one or more of any of the 11 peptide pools from the 4 antigens. The solid columns show response rates in TB patients, and the hatched columns show response rates in unexposed BCG-vaccinated donors.

FIG. 2 shows the magnitude of IFN-γ ELISPOT responses to RD region antigens in 49 culture confirmed TB patients (A) and 38 healthy, unexposed BCG vaccinees (B). Frequencies of peptide-specific IFN-γ-secreting spot-forming cells (SFCs) summated for each of the constituent peptide pools for each antigen, enumerated by ex vivo ELISPOT assay in patients with TB(A), and healthy, unexposed BCG vaccinated donors(B). The horizontal bars represent the median response for each antigen. Points on the baseline represent individuals with no response to a given antigen (ie less than 5 SFCs above the negative control for each of the constituent peptides of each pool of the given antigen). The broken horizontal line represents the predefined cutoff point (5 SFC per $2.5 \times 10^5$ PBMC, which translates into a threshold of detection of 20 peptide-specific T-cells per million PBMC).

FIG. 3 illustrates the location and homology of PPE protein family motif as described see the TubercuList World-Wide Web Server at the website for the Institut Pasteur), within the partial amino acid sequence of Rv3873 (amino acid residues 100-160) (SEQ ID NO:32 compared to SEQ ID NO:33). Amino acid residues are shown in the one letter code. Underlined residues indicate the given peptide sequence. Identical residues are indicated with a cross.

DETAILED DESCRIPTION OF THE INVENTION

The invention concerns diagnosis of tuberculosis infection in a human based on determination of whether the T cells of the human recognise an epitope of Rv3879c (SEQ ID NO:1). The method may also comprise determining whether T-cells of the human recognise one or more further *Mycobacterium tuberculosis* T-cell antigen(s), such as antigens encoded by the RD-1 or RD-2 region (preferably ESAT-6 and/or CFP10). In one embodiment the method comprises determining whether the T cell recognise one or more of the peptides represented by SEQ ID NO's 2 to 18.

The human who is tested typically has an active or latent mycobacterial infection, or has had such an infection recently. The human may test positive or negative in a Mantoux test. The human may be at risk of a mycobacterial infection, typically for socio-economic reasons or may have a genetic or acquired predisposition to mycobacterial infection.

The human may be a known or suspected contact who has been exposed to or may have been exposed to *Mycobacterium tuberculosis*. Typically the exposure is to pulmonary tuberculosis, such as 'open' pulmonary tuberculosis which is sputum A.F.B. (acid-fast *bacillus*) smear positive. Thus the method may be used to trace the healthy contacts of individuals with such tuberculosis infections. The method may also be used to carry out population surveys to measure the number of individuals in a population who have a *Mycobacterium tuberculosis* infection. The contact may be someone whose exposure is a household, work place (such as a health care worker) or prison exposure (such as a prisoner). The exposure may have resulted from residing in a country with high prevalence of TB, and diagnostic testing after emigration to a country with a low prevalence of TB. Thus the contact may be an immigrant.

The human who is tested (who has a known or suspected exposure) may be healthy or might have a chronic condition putting them at a higher risk of developing active TB and/or which may make TB infection harder to diagnose. Examples include HIV infected individuals, individuals taking immunosuppressants (e.g. corticosteroids, azathioprine and anti-TNF-α agents, such as infliximab, and cancer therapy), hemodialysis patients, organ transplant recipients, diabetics and very young children (aged under 5 years old, particularly under 2 years old).

The T cells which recognise the peptide in the method are generally T cells which have been pre-sensitised in vivo to antigen from a *M. tuberculosis*. These antigen-experienced T cells are generally present in the peripheral blood of a host which has been exposed to the *M. tuberculosis* at a frequency of 1 in $10^6$ to 1 in $10^3$ peripheralblood mononuclear cells (PBMCs). The T cells may be CD4 and/or CD8 T cells.

In the method the T cells can be contacted with the peptides in vitro or in vivo, and determining whether the T cells recognise the peptide can be done in vitro or in vivo. Thus the invention provides a method of diagnosis which is practised on the human body.

Determination of whether the T cells recognise the peptide is generally done by detecting a change in the state of the T cells in the presence of the peptide or determining whether the T cells bind the peptide (e.g. using an MHC tetramer combined with FACS analysis system), i.e. the method of the invention does not necessarily rely on the detection of a functional response of the T cell.

In the case where a change in state of the T cells is detected this is generally caused by antigen specific functional activity of the T cells after the T cell receptor binds the peptide. Generally when binding the T cell receptor the peptide is bound to an MHC class I or II molecule, which is typically present on the surface of an antigen presenting cell (APC).

The change in state of the T cell may be the start of or increase in secretion of a substance from the T cell, such as a cytokine, especially IFN-γ, IL-2 or TNF-α. Determination of IFN-γ secretion is particularly preferred. Intracellular cytokine detection by FACS may be used. The substance can typically be detected by allowing it to bind to a specific binding agent and then measuring the presence of the specific binding agent/substance complex. Detection of the substance may be carried out using an ELISA based system. The specific binding agent is typically an antibody, such as polyclonal or monoclonal antibodies. Antibodies to cytokines are commercially available, or can be made using standard techniques.

Typically the specific binding agent is immobilised on a solid support. After the substance is allowed to bind the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody which is immobilised on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below.

The change in state of the T cell which can be measured may be the increase in the uptake of substances by the T cell, such as the uptake of thymidine. The change in state may be an increase in the size of the T cells, or proliferation of the T cells, or a change in cell surface markers on the T cell.

Generally the T cells which are contacted in the method are taken from the host in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD4 or only CD8 T cells, can be purified from the sample. PBMCs, MCs and T cells can be separated from the sample using techniques known in the art, such as those described in Lalvani et al (1997) *J. Exp. Med.* 186, p 859-865.

Preferably the T cells used in the assay are in the form of unprocessed or diluted samples, or are freshly isolated T cells (such as in the form of freshly isolated MCs or PBMCs) which are used directly ex vivo, i.e. they are not cultured before being used in the method. However the T cells can be cultured before use, for example in the presence of one or more of the peptides, and generally also exogenous growth promoting cytokines. During culturing the peptides are typically present on the surface of APCs, such as the APC used in the method. Pre-culturing of the T cells may lead to an increase in the sensitivity of the method. Thus the T cells can be converted into cell lines, such as short term cell lines (for example as described in Ota et al (1990) *Nature* 346, p 183-187).

The APC which is typically present in the method may from the same host as the T cell or from a different host. The APC may be a naturally occurring APC or an artificial APC. The APC is a cell which is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

Typically in the method the T cells derived from the sample can be placed into an assay with all the peptides (i.e. a pool of the peptides) which it is intended to test (the relevant panel) or the T cells can be divided and placed into separate assays each of which contain one or more of the peptides. Preferably in the in vitro or in vivo forms of the method.

The invention also provides the peptides such as two or more of any of the peptides mentioned herein (for example in any of the combinations mentioned herein) for simultaneous, separate or sequential use (eg. for in vivo use).

In one embodiment peptide per se is added directly to an assay comprising T cells and APCs. As discussed above the T cells and APCs in such an assay could be in the form of MCs. When peptides which can be recognised by the T cell without the need for presentation by APCs are used then APCs are not required. Analogues which mimic the original peptide bound to a MHC molecule are an example of such a peptide.

In one embodiment the peptide is provided to the APC in the absence of the T cell. The APC is then provided to the T cell, typically after being allowed to present the peptide on its surface. The peptide may have been taken up inside the APC and presented, or simply be taken up onto the surface without entering inside the APC.

The duration for which the peptide is contacted with the T cells will vary depending on the method used for determining recognition of the peptide. Typically $10^5$ to $10^7$, preferably $5 \times 10^5$ to $10^6$ PBMCs are added to each assay. In the case where peptide is added directly to the assay its concentration is from $10^{-1}$ to $10^3$ µg/ml, preferably 0.5 to 50 µg/ml or 1 to 10 µg/ml.

Typically the length of time for which the T cells are incubated with the peptide is from 4 to 24 hours (preferably 6 to 16 hours) for effector T cells or for more than 24 hours for central memory cells. When using ex vivo PBMCs it has been found that $0.3 \times 10^6$ PBMCs can be incubated in 10 µg/ml of peptide for 12 hours at 37° C.

The method may be based on an ELISA method, such as the whole blood Quantiferon system and its modifications (for example as available from Cellestis).

The determination of the recognition of the peptide by the T cells may be done by measuring the binding of the peptide to the T cells. Typically T cells which bind the peptide can be sorted based on this binding, for example using a FACS machine. The presence of T cells which recognise the peptide will be deemed to occur if the frequency of cells sorted using the peptide is above a 'control' value. The frequency of antigen-experienced T cells is generally 1 in $10^6$ to 1 in $10^3$, and therefore whether or not the sorted cells are antigen-experienced T cells can be determined.

The determination of the recognition of the peptide by the T cells may be measured in vivo. Typically the peptide is administered to the host and then a response which indicates recognition of the peptide may be measured. In one embodiment the peptide is administered intradermally, typically in a similar manner to the Mantoux test. The peptide may be administered epidermally. The peptide is typically administered by needle, such as by injection, but can be administered by other methods such as ballistics, for example the ballistics techniques which have been used to deliver nucleic acids. EP-A-0693119 describes techniques which can typically be used to administer the peptide. Typically from 0.001 to 1000 µg, for example from 0.01 to 100 µg or 0.1 to 10 µg of peptide is administered.

Alternatively an agent can be administered which is capable of providing the peptides in vivo. Thus a polynucleotide capable of expressing the peptide can be administered, typically in any of the ways described above for the administration of the peptide. The polynucleotide typically has any of the characteristics of the polynucleotide provided by the invention which is discussed below. Peptide is expressed from the polynucleotide in vivo and recognition of the peptide in vivo is measured. Typically from 0.001 to 1000 µg, for example from 0.01 to 100 µg or 0.1 to 10 µg of polynucleotide is administered.

Recognition of the peptide in vivo is typically indicated by the occurrence of a DTH response. This is generally measured by visual examination of the site of administration of the peptide to determine the presence of inflammation, such as by the presence of induration, erythema or oedema.

The peptide capable of binding to a T-cell receptor which recognises a peptide having the sequence shown in SEQ ID NO:1 or any other peptides to be tested (i.e. analogues of the peptide) may be identified by any suitable method. The binding of the peptide to the said T cell receptors can be tested by standard techniques. For example, T cell receptors can be isolated from T cells which have been shown to recognise the peptide having a sequence shown in SEQ ID NO:1 (e.g. using the method of the invention). Demonstration of the binding of the peptide to the T cell receptors can then shown by determining whether the T cell receptors inhibit the binding of the peptide to a substance that binds the peptide, e.g. an antibody to the peptide. Typically the peptide is bound in an MHC molecule in such an inhibition of binding assay.

Typically the analogue inhibits the binding of the peptide to a T cell receptor. In this case the amount of peptide which can bind the T cell receptor in the presence of the analogue is decreased. This is because the analogue is able to bind the T cell receptor and therefore competes with the peptide for binding to the T cell receptor.

T cells for use in the above binding experiments can be isolated from patients with mycobacterial infection, for example with the aid of the method of the invention.

The analogue may have homology with the equivalent original peptide represented by one of SEQ ID NO:1 or a sequence of at least 8 consecutive amino acids of SEQ ID NO:1. A peptide which is homologous to another peptide is typically at least 70% homologous to the peptide, preferably at least 80 or 90% and more preferably at least 95%, 97% or 99% homologous thereto, for example over a region of at least 8, at least 15, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology"). For example the UWGCG Package provides the BESTFIT, program which can be used to calculate homology (for example used on its default settings) (Devereux et al (1984) *Nucleic Acids Research* 12, p 387-395).

Typically the amino acids in the analogue at the equivalent positions to amino acids in the original peptide which contribute to binding the MHC molecule or are responsible for the recognition by the T cell receptor, are the same or are conserved.

Typically the analogue comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The peptide may comprise one or more non-natural amino acids, for example amino acids with a side chain different from natural amino acids. Generally, the non-natural amino acid will have an N terminus and/or a C terminus. The non-natural amino acid may be an L-amino acid.

The peptide typically has a shape, size, flexibility or electronic configuration which is substantially similar to the original peptide. It is typically a derivative of the original peptide.

In one embodiment the peptide is or mimics the original peptide bound to a MHC class II molecule. The analogue may be or may mimic the original peptide bound to 2, 3, 4 or more MHC class II molecules associated or bound to each other. These MHC molecules may be bound together using a biotin/streptavidin based system, in which typically 2, 3 or 4 biotin labelled MHC molecules bind to a streptavidin moiety. This peptide typically inhibits the binding of the peptide/MHC Class II complex to a T cell receptor or antibody which is specific for the complex. The analogue may be an antibody or a fragment of an antibody, such as a Fab or (Fab)$_2$ fragment.

The peptide may be immobilised on a solid support.

The peptide is typically designed by computational means and then synthesised using methods known in the art. Alternatively it can be selected from a library of compounds. The library may be a combinatorial library or a display library, such as a phage display library. The library of compounds may be expressed in the display library in the form of being bound to a MHC class II molecule, such as the MHC molecule which the original peptide binds. Peptides are generally selected from the library based on their ability to mimic the binding characteristics of the original peptides. Thus they may be selected based on ability to bind a T cell receptor or antibody which recognises the original peptide.

The invention also provides a kit for carrying out the method comprising one or more of the peptides and a means to detect the recognition of the peptide by the T cell. Typically the peptides are provided for simultaneous, separate or sequential use. Typically the means to detect recognition allows or aids detection based on the techniques discussed above.

Thus the means may allow detection of a substance secreted by the T cells after recognition. The kit may thus additionally include a specific binding agent for the substance, such as an antibody. The agent is typically specific for IFN-γ. The agent is typically immobilised on a solid support. This means that after binding the agent the substance will remain in the vicinity of the T cell which secreted it. Thus 'spots' of substance/agent complex are formed on the support, each spot representing a T cell which is secreting the substance. Quantifying the spots, and typically comparing against a control, allows determination of recognition of the peptide.

The kit may also comprise a means to detect the substance/agent complex. A detectable change may occur in the agent itself after binding the substance, such as a colour change. Alternatively a second agent directly or indirectly labelled for detection may be allowed to bind the substance/agent complex to allow the determination of the spots. As discussed above the second agent may be specific for the substance, but binds a different site on the substance than the first agent.

The immobilised support may be a plate with wells, such as a microtitre plate. Each assay can therefore be carried out in a separate well in the plate.

The kit may additionally comprise medium for the T cells, detection agents or washing buffers to be used in the detection steps. The kit may additionally comprise reagents suitable for the separation from the sample, such as the separation of PBMCs or T cells from the sample. The kit may be designed to allow detection of the T cells directly in the sample without requiring any separation of the components of the sample.

The kit may comprise an instrument which allows administration of the peptide, such as intradermal or epidermal administration. Typically such an instrument comprises one or more needles. The instrument may allow ballistic delivery of the peptide. The peptide in the kit may be in the form of a pharmaceutical composition.

The kit may also comprise controls, such as positive or negative controls. The positive control may allow the detection system to be tested. Thus the positive control typically mimics recognition of the peptide in any of the above methods. Typically in the kits designed to determine recognition in vitro the positive control is a cytokine. In the kit designed to detect in vivo recognition of the peptide the positive control may be antigen to which most individuals should response.

The kit may also comprise a means to take a sample containing T cells from the human, such as a blood sample. The kit may comprise a means to separate mononuclear cells or T cells from a sample from the human.

The invention also provides a composition comprising a peptide of the invention. The composition may be a pharmaceutical composition which further comprises a pharmaceutically acceptable carrier or diluent. Suitable carriers and diluents include isotonic saline solutions, for example phosphate-buffered saline. Typically the composition is formulated for intradermal or epidermal administration or for application by ballistic techniques. Thus the peptide or polynucleotide may be associated with a carrier particle for ballistic delivery.

The invention also relates to a polynucleotide which is capable of expressing one or more peptides of the invention. Typically the polynucleotide is DNA or RNA, and is single or double stranded. The polynucleotide therefore typically comprises sequence which encodes the sequence of SEQ ID NO: 1 or a fragment thereof.

5' and/or 3' to the sequence encoding the peptide the polynucleotide has coding or non-coding sequence. Sequence 5' and/or 3' to the coding sequence may comprise sequences which aid expression, such as transcription and/or translation, of the sequence encoding the peptide. The polynucleotide may be capable of expressing the peptide in a prokaryotic or eukaryotic cell. In one embodiment the polynucleotide is capable of expressing the peptide in a mammalian cell, such as a human, primate or rodent cell.

The polynucleotide may be incorporated into a replicable vector. Such a vector is able to replicate in a suitable cell. The vector may be an expression vector. In such a vector the polynucleotide of the invention is operably linked to a control sequence which is capable of providing for the expression of the polynucleotide. The vector may contain a selectable marker, such as the ampicillin resistance gene.

The polynucleotide of the invention, the peptides in a composition of the invention or the agents used in the method (for example in the detection of substances secreted from T cells) may carry a detectable label. Detectable labels which allow detection of the secreted substance by visual inspection, optionally with the aid of an optical magnifying means, are preferred. Such a system is typically based on an enzyme label which causes colour change in a substrate, for example alkaline phosphatase causing a colour change in a substrate. Such substrates are commercially available, e.g. from Bio-Rad. Other suitable labels include other enzymes such as peroxidase, or protein labels, such as biotin; or radioisotopes, such as $^{32}P$ or $^{35}S$. The above labels may be detected using known techniques.

Polynucleotides of the invention or peptides in a composition of the invention may be in substantially purified form. They may be in substantially isolated form, in which case they will generally comprise at least 90%, for example at least 95, 97 or 99% of the polynucleotide, peptide or antibody in the preparation. The substantially isolated peptides generally comprise at least 90%, such as for example at least 95, 97 or 99% of the dry mass of the preparation. The polynucleotide or peptide are typically substantially free of other cellular components or substantially free of other mycobacterial cellular components. The polynucleotide or peptide may be used in such a substantially isolated, purified or free form in the method or be present in such forms in the kit.

The peptide for use in the invention can be made using standard synthetic chemistry techniques, such as by use of an automated synthesizer.

The peptide is typically made from a longer polypeptide e.g. a fusion protein, which polypeptide typically comprises the sequence of the peptide. The peptide may be derived from the polypeptide by for example hydrolysing the polypeptide, such as using a protease; or by physically breaking the polypeptide. The polypeptide typically has the sequence shown in SEQ ID NO:1 and may have been expressed recombinantly.

The peptide can also be made in a process comprising expression of a polynucleotide, such as by expression of the polynucleotide of the invention. The expressed polypeptide may be further processed to produce the peptide of the invention. Thus the peptide may be made in a process comprising cultivating a cell transformed or transfected with an expression vector as described above under conditions to provide for expression of the peptide or a polypeptide from which the peptide can be made. The polynucleotide of the invention can be made using standard techniques, such as by using a synthesiser.

The invention also provides a method of ascertaining the stage of a *Mycobacterium tuberculosis* infection in a human comprising determining whether there is a differential T cell response to different MTB antigens in the human. Any suitable method mentioned herein may be used to measure the T cell responses. The T cell responses may be to any of the MTB antigens mentioned herein, such as one or more of Rv3879c, ESAT-6, CFP10, Rv3873, Rv3878, Rv1989c. The method may be carried out to determine whether the infection is recent or longstanding, to determine whether the human is latently infected or has disease, or to monitor the effect of treatment.

The invention is illustrated by the following Examples:

Example 1

Study Participants

All participants were recruited prospectively in London and Oxford over a 14 month period from June 2002 through July 2003. Ethical approval for the study was granted by the Harrow and Central Oxford Research Ethics Committees. The diagnoses of all 49 TB patients were bacteriologically confirmed with positive cultures for MTB from one or more clinical specimens. Patients were untreated or had received less than 2 weeks therapy at the time of venipuncture for ELISPOT assay. Control participants were healthy BCG-vaccinated laboratory personnel from regions with a low prevalence of TB and with no known exposure to MTB. All had recently tested negative by IFN-γ-ELISPOT using 38 overlapping 15-mer peptides spanning the length of ESAT-6 and CFP10, as previously described (Lalvani et al. 1997. J. Exp. Med. 186:859-865).

Epidemiological data regarding place of birth, any period of residence in higher prevalence regions and absence of TB contact was collected from these volunteers at the point of venepuncture. Health care workers were not recruited due to the risk of occupational TB exposure.

Peptides

Sixty-seven synthetic peptides spanning selected regions of four open reading frames (ORFs) were designed and purchased (Research Genetics, Huntsville, Ala., USA). The peptides were selected from those used in (Cockle et al. 2002 Infect. Immunol. 70:6996-7003). The Rv3879c peptides are 15mer peptides overlapping by 10 amino acids which represent 95 out of 729 amino acids of the Rv3879c primary amino acid sequence. This selection of peptides represents only 13% of the entire sequence of Rv3879c.

In the case of all four molecules except Rv3873, these sequences were at the amino terminus, and the exact regions represented by the peptides for each molecule are shown in table 2. Each peptide was 15 residues long and overlapped the adjacent peptide by 10 amino acids (a.a.). This approach has previously been shown to be effective for detecting HLA class I-restricted CD8 as well as HLA class II-restricted CD4 T cell responses (Pathan et al. 2000. Eur. J. Immunol. 30:2713-2721). The 67 peptides were arranged into 11 pools containing between five and seven peptides and Table 2 shows the pools in relation to the antigens they represent. For all peptides, identity was confirmed by mass spectrometry and purity was more than 70%.

Ex Vivo IFN-γ ELISPOT Assays

ELISPOT assays were performed as previously described (Lalvani et al. 1997. J. Exp. Med. 186:859-865 Lalvani et al.

2001. Am. J. Respir. Crit. Care. Med. 163: 824-828). IFN-γ-ELISPOT plates (Mabtech AB, Stockholm, Sweden), were seeded with 2.5×10⁵ PBMCs per well: duplicate wells contained no antigen (negative control), phytohaemagglutinin (PHA, positive control, ICN Biomedical Ohio, USA), at 5 μg/ml, streptokinase/streptodornase (SKSD, Varidase, Cyanamid, Hampshire, UK) at 100 u/ml, Purified Protein Derivative (PPD, Statens Serum Institut, Denmark) at 20 μg/ml, and one of 11 peptide pools, such that the final concentration of each peptide was 10 μg/ml. After overnight incubation at 37° C., 5% $CO_2$, the plates were developed with preconjugated detector antibody and chromogenic substrate, 5-bromo-4-chloro-3-indolyl-phosphate p-nitro blue tetrazolium chloride (BCIP/NBT plus, Moss Inc, Pasadena, Md., USA). For unexposed BCG-vaccinated donors who responded to any of the pools, PBMC were retested against all 67 peptides individually in single ELISPOT wells at a final concentration of 10 μg/ml.

Assays were scored by an automated ELISPOT counter (AID-GmbH, Strassberg, Germany). For wells containing peptide pools, responses were scored as positive if the test well contained at least five more IFN-γ spot-forming cells (SFC) than negative control wells and this number also had to be at least twice the frequency found in the negative control wells. These pre-defined cut-off points translate into a detection threshold of 20 peptide-specific T cells per million PBMC. The person performing the assays was blind to personal identifiers of participants.

Bioinformatics

The DNA sequence of MTB H37Rv was visualized using the TubercuList database (see the world wide website of the Institut Pasteur) Basic Local Alignment Search Tool (BLAST) searches for protein sequence homology in available mycobacterial genomes were performed using TubercuList, the Sanger Centre server (Cambridge, UK) for the incomplete *M. Bovis* BCG genome sequence (see the world wide website of the Sanger Centre) and the National Center for Biotechnology Information (NCBI) BLAST server (see the world wide website of the NCBI).

Example 2

Demographic Characteristics of Study Participants

Demographic characteristics of the 49 culture-confirmed TB patients are shown in Table 1. 42 patients had pulmonary TB, of whom 23 were sputum smear-positive. The 7 patients with extra-pulmonary TB, comprised patients with pleural TB (n=3); lymphadenitis (n=1), miliary TB (n=2) and urinary tract TB (n=1). The patients were from a broad range of ethnicities. Demographic characteristics of BCG donors are shown in Table 1. All donors were born in regions of low prevalence for TB (Europe or Australia). None had a history of known TB contact and none had resided for more then 3 months in high prevalence regions.

Example 3

Figure 1B:
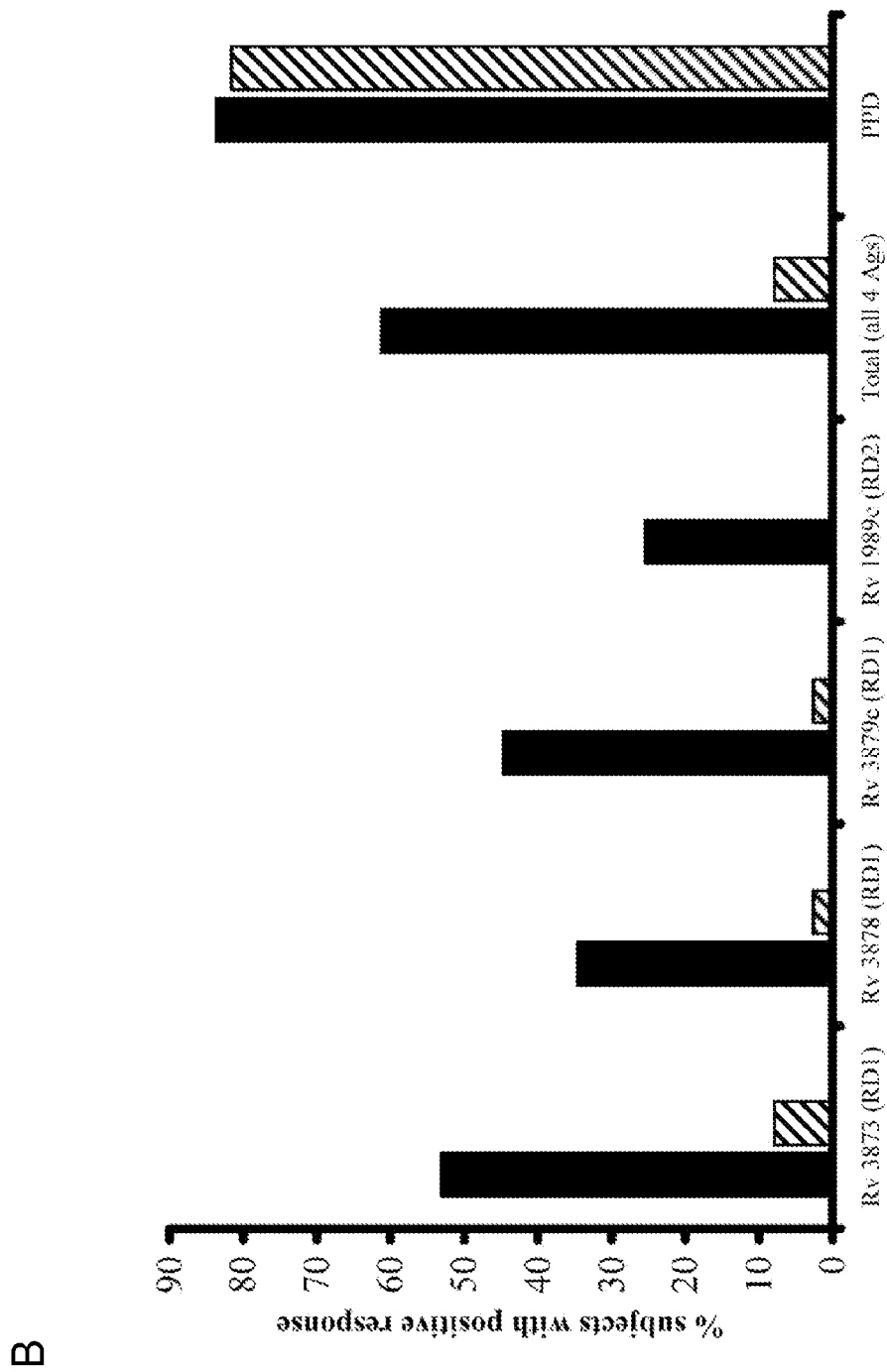

IFN-γ ELISPOT Responses to Peptides from Rv3873, Rv3878, Rv3879c and Rv1989c in Culture-Confirmed Tuberculosis Patients IFN-γ ELISPOT responses of PBMC from all 49 TB patients to the 11 peptide pools from the four antigens are summarized in FIG. 1A. The percentages of responding patients varied between 25.5% and 53.1% for the different antigens (FIG. 1B). The proportion of patients responding to peptides from each of the antigens Rv3873, Rv3879c, Rv3878 and Rv1989c was 53.1% (95% CI 39-67%), 44.7% (95% CI 31-57%), 34.7% (95% CI 22-48%) and 25.5% (95% CI 13-39%), respectively (FIG. 1B). Combining these responses, 30 of 49 tuberculosis patients responded to peptide pools from one or more antigens, giving a diagnostic sensitivity of 61.2% (95% confidence interval [CI] 46.2%-74.8%) for all peptides used together. This contrasts with the results obtained by Cockle et al. 2002 Infect. Immunol. 70:6996-7003, who found that peptides from Rv3873, Rv3878, Rv3879c, Rv1989c could together be used to detect almost all infected cattle.

Figure 2A:
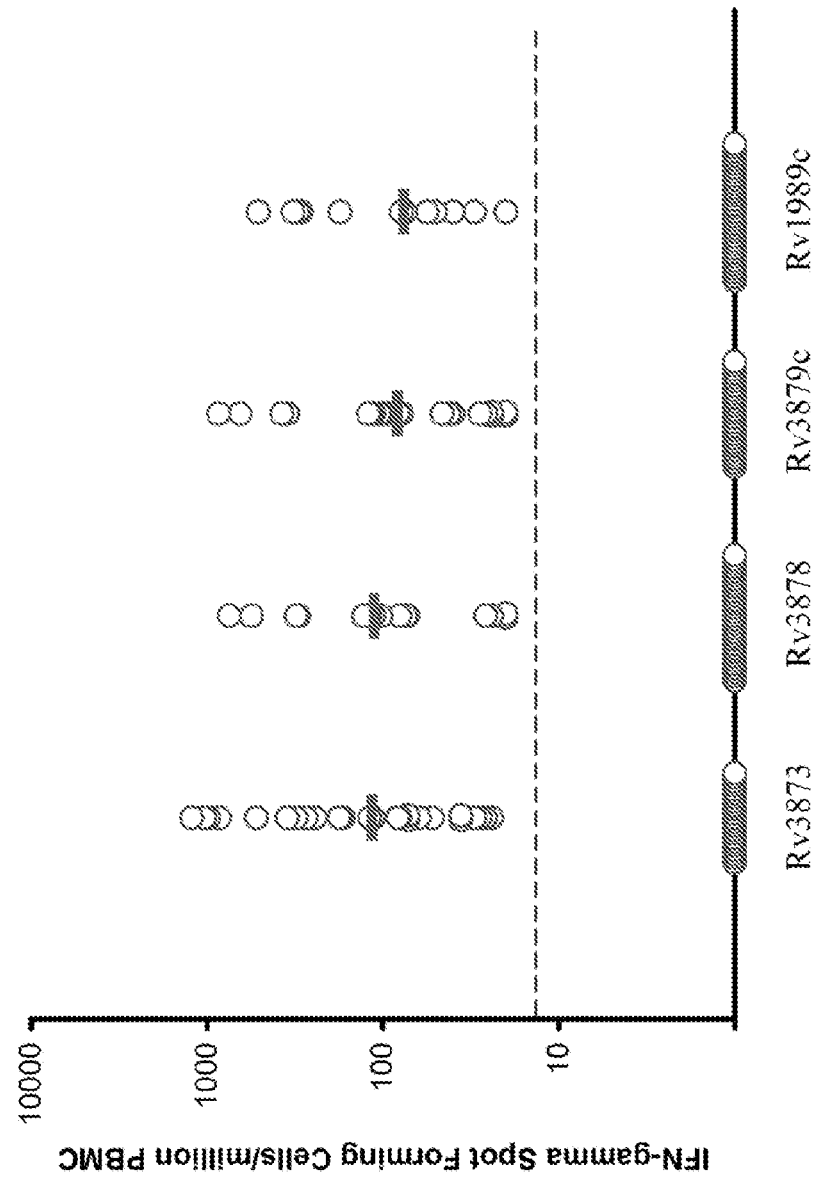

The frequencies of Rv3873, Rv3878, Rv3879c, Rv1989c peptides-specific IFN-γ-secreting T cells for all responder patients were (median response and inter quartile ranges [IQR]): 115 [52 to 310], 112 [72 to 128], 82 [28 to 116], and 76 [45 to 296] per million PBMCs, respectively (FIG. 2A).

Importantly, 3 of the 49 TB patients who responded to Rv3879c peptides failed to respond to any of 35 15mer peptides representing the entire sequences of ESAT-6 and CFP10.

Example 4

Comparison of Proportions of Patients Responding to Each Antigen According to the Clinical Type of TB The TB patients were stratified by clinical type of TB, i.e. pulmonary (n=42) versus extra-pulmonary (n=7) TB. The proportion of patients from each group that responded to peptides from each different protein were then compared. Although there was no significant difference between the proportion of pulmonary and extra-pulmonary patients that responded to Rv3873, Rv3878 and Rv1989c, significantly more extra-pulmonary patients (6/7, 86%) responded to Rv3879c than did pulmonary patients (14/42, 33%), (p=0.014).

Example 5

IFN-γ ELISPOT Responses in BCG-Vaccinated Healthy Donors

Rv3873 peptide pools elicited responses in 3/38 (7.9%) BCG-vaccinated unexposed donors; Rv3878 and Rv3879c each elicited a response in one (2.6%) donor; and Rv1989c elicited no responses. Two donors, donors 20 and 31, each responded to a different peptide from pool 2 of Rv3873, and one, donor 25, responded to pools from the Rv3873, Rv3878 and Rv3879c (Table 2 and FIG. 1). Donors 20 and 31 responded to peptides 119-133 (LTATNFFGINTIPIA; SEQ ID No 21) and 139-153 (YFIRMWNQAALAMEV; SEQ ID No 22), respectively, both from pool 2 of Rv3873. Donor 25 responded to peptide 174-188 (LDPGASQSTTNPIFG; SEQ ID No 23) from Rv3873, peptides 16-30 (AAKLAGLVF-PQPPAP; SEQ ID No 24) and 61-75 (ESLVSDGLPGV-KAAL; SEQ ID No 25) from Rv3878 and 26-40 (DTFY-DRAQEYSQVLQ; SEQ ID No 7) from Rv3879c. Combining all these responses, 3 of 38 (7.9%) BCG vaccinated healthy donors responded to one or more antigens, while 81.6% responded to PPD.

Figure 2B:
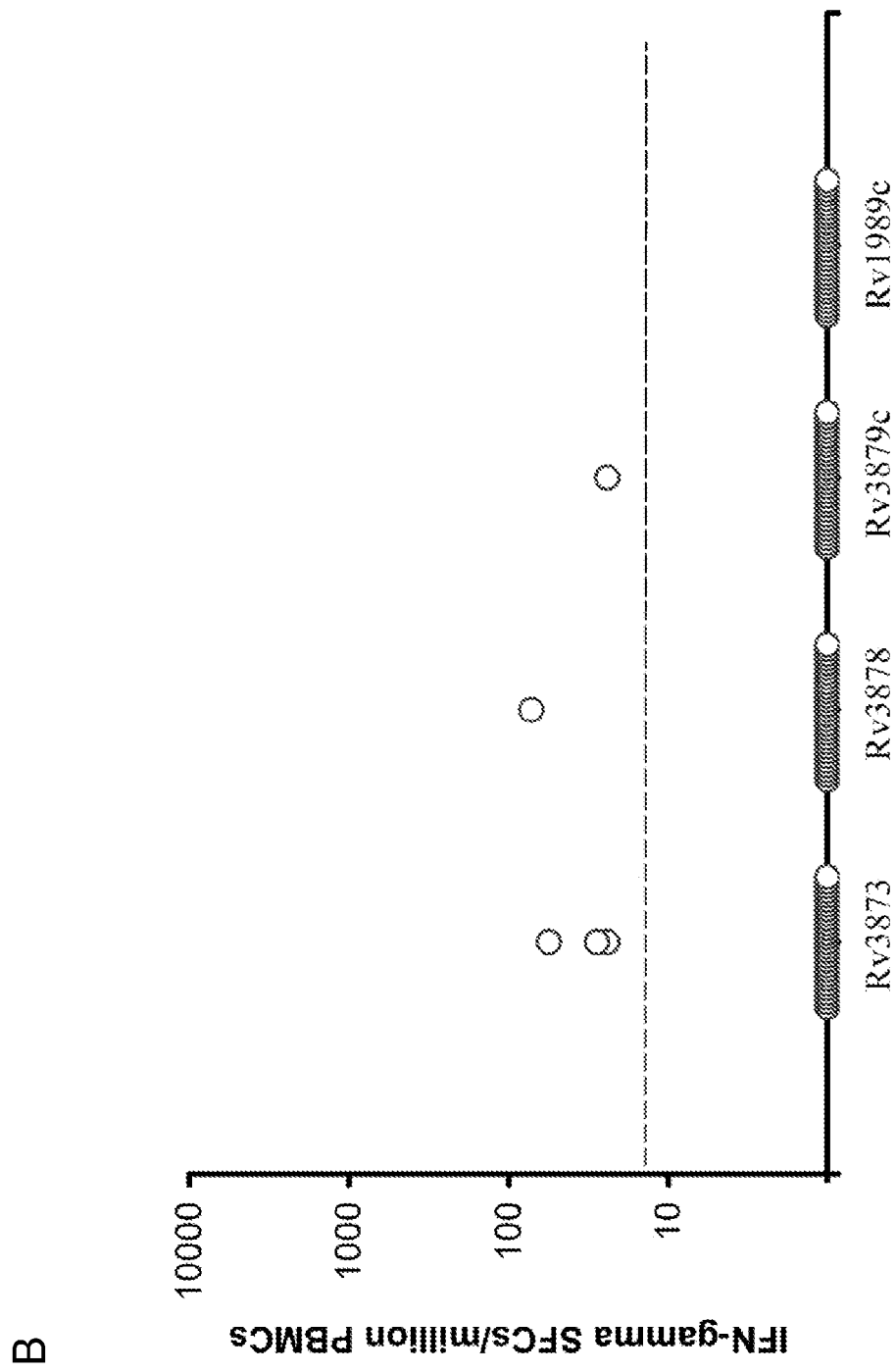

The frequencies of peptide specific IFN-γ SFCs seen in BCG-vaccinated unexposed donors were much lower than in the TB patients (FIG. 2B). The median frequencies of peptide-specific T cells (and inter-quartile range) were: 28 (24 to 56), 72 (72) and 20 (20) per million PBMC for Rv3873, Rv3878 and Rv3879c respectively (FIG. 2A).

Example 6

BLAST Searches of Cross-Reactive Peptide Sequences

BLAST searches for protein sequences highly homologous to the six 15mer peptides that gave a response in BCG-vaccinated donors were performed. Peptide 119-133 (LTAT- NFFGINTIPIA; SEQ ID No 21), had the greatest homology with 93% identity to other mycobacterial proteins (14 out of 15 amino acids identical). This peptide is from pool 2 of Rv3873, a member of the PPE family of proteins, and is encoded within a 52 a.a. long motif that is highly conserved throughout the PPE family (FIG. 3). Consequently it displays high levels of homology with many MTB, M. bovis and M. leprae PPE proteins (Table 3) that are encoded in the deleted and undeleted regions of the genomes of MTB, M. bovis and other mycobacteria. Peptide 139-153 (YFIRMWN-QAALAMEV; SEQ ID No 22), which is also encoded within the 52 a.a. conserved motif of Rv3873 (FIG. 3), also showed homology with sequences from many PPE proteins (Table 3) although the level of identity was considerably lower at 47% (7 out of 15 identical residues). In contrast, peptide 174-188 (LDPGASQSTTNPIFG; SEQ ID No 23) from Rv3873, which lies outside the conserved motif region, had no significant homology with PPE family members. The two cross-reactive peptides from Rv3878 and the single cross-reactive peptide from Rv3879c, had no significant sequence homology with any other mycobacterial proteins.

Discussion

We have evaluated human cellular immune responses to peptide mixtures of four MTB proteins encoded in regions of difference RD1 and RD2. This is the first such report for Rv3879c and Rv1989c; for Rv3873 and Rv3878 cellular immune responses were also recently described by Okkels et al (2003. Infect. Immun. 71: 6116-23). Peptides from each protein were recognized by T cells from >25% of TB patients in IFN-γ-ELISPOT assays. Peptide pools from two RD1-encoded gene products were recognized in approximately half of all TB patients tested: Rv3879c (45%) and the PPE family member Rv3873 (53%). This study thus identifies these two proteins as major MTB T cell antigens in infected humans. IFN-γ-ELISPOT responses to the peptides were rare in BCG-vaccinated donors, giving a specificity of 97.4% or more for all antigens except Rv3873, which, on account of cross-reactive peptides from conserved sequences, had a lower specificity of 92.1%. The high specificity of the Rv3879c peptides (97.4%), together with the fact that they are recognized in IFN-γ-ELISPOT by almost a half of TB patients, identifies this molecule as a useful T cell antigen for inclusion in novel T cell-based diagnostic tests of MTB infection.

CMI to the antigens in this study has previously been assessed in cattle (Cockle et al. 2002 Infect. Immunol. 70:6996-7003). Despite being encoded in RD1, peptides derived from Rv3873 and Rv3879c elicited IFN-γ responses in a whole blood ELISA assay in 17% and 33% of BCG-vaccinated cattle respectively. However, the responses were only borderline positive, and the number of vaccinated cattle tested was low (n=6). In our larger series of BCG-vaccinated humans, we have shown that the level of cross-reactivity of these antigens with BCG is far lower than in cattle. Moreover, 3 of the 5 responses observed were borderline positive (FIG. 2B).

T cell responses to peptides spanning the length of ESAT-6/CFP10 have been detected in 70-80% of TB patients using IFN-γ ELISA and around 90% of TB patients using IFN-γ-ELISPOT assay. We have shown that T cell responses to Rv3879c peptides also occur in MTB infected humans, and further that some culture confirmed TB patients who failed to respond to ESAT-6 and CFP10 peptides did respond Rv3879c peptides. Thus Rv3879c peptides may be used to further enhance the sensitivity of T cell-based assays using ESAT-6/CFP10, without compromising specificity.

TABLE 1

Demographic characteristics of TB patients and unexposed BCG-vaccinated donors

|  | Patients with tuberculosis (n = 49) (%) | BCG donors (n = 38) (%) |
|---|---|---|
| Mean age in years(range) | 34.0 ± 13.4(17-78) | 33.3 ± 6.7(20-50) |
| Sex (male/female) | 31/18(63/37) | 22/16(58/42) |
| Ethnicity |  |  |
| Indian Sub-Continent | 24(49) | 1 |
| African | 18(37) | 0 |
| Oriental | 4(8) | 0 |
| White | 3(6) | 37 |

TABLE 2

Antigens and peptide pools evaluated and number of donors who responded to each peptide pool by IFN-γ-ELISPOT assay

| Region of Difference | Designation | Size (amino acids) | Putative Function[c] | Peptide Pools (no. of constituent peptides) | Region of molecule represented by peptide pools (aa position) | No. TB patients responding n = 49 | No. unexposed BCG vaccinated donors responding n = 38 |
|---|---|---|---|---|---|---|---|
| RD1 | Rv 3873 | 368 | Member of the M. TB PPE family | Pool 1 (6) | 89-128 | 8 | 0 |
|  |  |  |  | Pool 2 (6) | 129-158 | 25 | 2 |
|  |  |  |  | Pool 3 (6) | 159-188 | 18 | 1 |
|  | Rv 3878 | 280 | Unknown alanine rich protein | Pool 1 (7) | 1-45 | 16 | 1 |
|  |  |  |  | Pool 2 (7) | 36-80 | 14 | 1 |
|  | Rv 3879c | 729 | Unknown alanine and proline rich protein | Pool 1 (6) | 1-40 | 12[a] | 1 |
|  |  |  |  | Pool 2 (6) | 31-70 | 18[a] | 0 |
|  |  |  |  | Pool 3 (5) | 61-95 | 9[b] | 0 |
| RD2 | Rv 1989c | 186 | Unknown | Pool 1 (6) | 1-40 | 10[b] | 0 |
|  |  |  |  | Pool 2 (6) | 31-70 | 7[b] | 0 |
|  |  |  |  | Pool 3 (6) | 61-100 | 8[b] | 0 |

[a]n = 48
[b]n = 47
[c]Putative function as suggested by Cole et al. 1998. Nature 393: 537-544

TABLE 3

Homology between peptides 119-133 and 139-153 from Rv3873 with sequences from other mycobacterial proteins.

| Designation[a] | Putative Function | Amino Acid Sequence[b] |
|---|---|---|
| (i) Peptide 119-133 | | |
| Rv3873 | M. tuberculosis PPE family | LTATNFFGINTIPIA; SEQ ID No 21 |
| Rv3021c, 3018c, 0280, 1387 | M. tuberculosis PPE family | L_V_ATNFFGINTIPIA; SEQ ID No 26 |
| Rv0256c | M. tuberculosis PPE family | L_M_ATNFFGINTIPIA; SEQ ID No 27 |
| Rv0453 | M. tuberculosis PPE family | _MV_ATNFFGINTIPIA; SEQ ID No 28 |
| (ii) Peptide 139-153 | | |
| Rv3873 | M. tuberculosis PPE family | YFIRMWNQAALAMEV SEQ ID No 22 |
| Rv2768c, 1039c | M. tuberculosis PPE family | H_YGE_MW_A_QD_ALAM_YG SEQ ID No 29 |
| Rv0286 | M. tuberculosis PPE family | D_YV_RMWL_Q_AA_AV_MGL SEQ ID No 30 |
| Rv1807 | M. tuberculosis PPE family | Q_YA_EMW_SQ_D_A_M_A_M_YG SEQ ID No 31 |

The homology search was performed using the BLAST program.
[a] Designation of M. tuberculosis proteins as described. Sequences of all related proteins described are also present in the M. bovis BCG genome (see the world wide website of the Sanger Centre). Non-identical residues are underlined.
[b] Amino acid residues are shown in the one letter code.

The homology search was performed using the BLAST program.

Example 7

Further Work 929 child (<16 yrs) household contacts of sputum smear positive pulmonary TB patients in Istanbul, Turkey (TB prevalence of 41/100,000) were recruited. All children underwent a Mantoux test, clinical assessment, chest x-ray and had a 10 ml blood sample taken for RD1 and RD2 based IFN-γELISPOT assay using purified, whole recombinant antigen from ESAT-6 and CFP10; and peptides (15mers overlapping by 10) from ESAT-6, CFP10, Rv3873, Rv3878, Rv3879c and Rv1989c (see Table 2 for the exact region of the molecule which was represented in the IFNγ ELISPOT assay). Demographic data was also collected including age, sex and BCG status with peptide-pools derived from Rv3873, Rv3878, Rv3879c and Rv1989c.

Table 4 shows the proportion of child household contacts that responded to ESAT-6/CFP10 antigens and peptides, and the Pools. Table 4a shows that 46.6% (95% CI 43.5%-49.7%) of all contacts responded to ESAT-6/CFP10 antigens, or peptides derived from the antigens, compared to 53.2% (95% CI 50.1%-56.3%) responding to any of the Pools. Omitting Pool 2 of Rv3873 responses, which are known to be cross-reactive with BCG (Liu et al (2004) Infect Immun. 72 p 2574-81) (see Table 3 and FIGS. 1 and 3), the response rate is decreased to 43.1% (95% CI 40.0%-46.2%). Response rates are further reduced when responses to RD2 derived Pools are removed, thus reducing the proportion of responders to 31.9% (95% CI 29.0%-34.8%). Table 4b illustrates how the responses were divided between the different antigens.

Of particular note, 150 (when excluding Pool 2 of Rv3873 responses) of the 494 contacts who responded to the Pools, were negative to ESAT-6 and CFP10, i.e. were only positive to a Pool. From Table 5a we can see what these patients were responding to. Table 5b illustrates the responses of patients who only responded to peptides from one of the novel antigens. Rv1989c has the greatest number of responses within this group with 63 patients responding to it exclusively.

Liu et al's findings indicated that Rv3873, Rv3878, Rv3879c and Rv1989c, excluding Pool 2 of Rv 3873 which contained the highly conserved PPE motifs, were highly specific in the population in which it was tested. This includes Rv1989c even though it is taken from RD2 which is present in some strains of BCG. It is therefore a valid assumption that they are also highly specific in this population, due to our knowledge of the BCG status of the population.

This population had an estimated BCG vaccination rate of 78.5%, and the strain of BCG used in Turkey is Pasteur 1173-P2. We can be confident that this strain of BCG does not contain RD2, and hence the responses to Rv1989c peptides are very probably M. tb specific and unlikely to be due to cross-reactivity within the BCG vaccinated individuals.

Although in this particular population it is valid to study and use Rv1989c derived responses, this is not the case for all populations as RD2 is present in some strains of BCG that are currently in use. To ensure the test can be used universally, it is prudent to remove pools derived from Rv1989c, the RD2 derived antigen. This leaves 77 patients who only responded to the New Pools, excluding Pool 2 of Rv3873 and pools 1, 2 and 3 of Rv 1989c.

6 months post exposure, patients were re-bled and a repeat IFN-γ ELISPOT was carried out. Of those 77 contacts who initially only responded to a Pool, as described above, 49% gave a positive response to either ESAT-6 or CFP10, with 43% still giving a negative response and data not available for 9%, as can be seen in Table 6. Given that the ESAT-6/CFP10 based IFN-γ ELISPOT is believed to be the new gold standard for detecting LTBI, the fact that 49% of recently exposed contacts who were initially ESAT-6/CFP10 IFN-γ ELISPOT negative but Pool IFN-γ ELISPOT positive suggests that responses to Pools may be a highly sensitive indicator of early M. tb infection.

Conclusions

These results show that the Pools, when used in the IFN-γ ELISPOT assay:
a) detect latent M. tb infection;
b) significantly increase sensitivity of the ESAT-6/CFP-10 based IFN-γ ELISPOT for detection of latent TB infection (150/433~34%);
c) enable earlier detection of asymptomatic M. tb infection in recently exposed contacts (77 of 510 contacts (15%) who gave a response to ESAT-6/CFP10 or the Pools excluding Pool 2 of Rv3873 and Pools 1 to 3 of Rv1989c only responded to the Pools with 49% of the 77 becoming ESAT-6/CFP10 positive 6 months after exposure to M. tb).

TABLE 4a

Percentage of Contacts with IFN-γ-ELISPOT Responses to the Pools (n = 929)

| | |
|---|---|
| ESAT6/CFP10 (antigens/peptides) | 46.6 |
| Pools | 53.2 |
| Pools excluding Pool 2 of Rv3873 | 43.1 |
| Pools excluding Pool 2 of Rv3873 and Pools 1 to 3 of 1989c | 31.9 |
| ESAT 6/CFP10 (antigensgs/peptides) and Pools excluding Pool 2 of Rv 3873 | 62.8 |

TABLE 4b

IFN-γ ELISPOT Responses to Each Antigen (n = 929)
(Shown as number of patients responding)

| | |
|---|---|
| Rv 3873 (Pools 1 to 3) | 370 |
| Rv 3878 (Pools 1 and 2) | 184 |
| Rv 3879c (Pools 1 to 3) | 224 |
| Rv 1989c (Pools 1 to 3) | 263 |

TABLE 5a

IFN-γ ELISPOT Response Frequencies For Each Antigen of Those Who Only responded to The Pools (Excluding Pool 2 of Rv 3873) (n = 150)

| | |
|---|---|
| Rv 3873 (Pools 1 and 3) | 52 |
| Rv 3878 (Pools 1 and 2) | 35 |
| Rv 3879c (Pools 1 to 3) | 53 |
| Rv 1989c (Pools 1 to 3) | 107 |

TABLE 5b

Contacts Who Only Responded to the Pools and Only One Region Within the Pools

| | |
|---|---|
| Rv 3873 (Pools 1 and 3) | 9 |
| Rv 3878 (Pools 1 and 2) | 2 |
| Rv 3879c (Pools 1 to 3) | 8 |
| Rv 1989c (Pools 1 to 3) | 63 |

TABLE 6

Percentage Responses at 6 months follow-up to ESAT and CFP10 in the IFN-γ-ELISPOT for those contacts who only responded to the pools excluding Pool 2 of Rv 3873 and Pools 1 to 3 of Rv 1989c at time zero (n = 77)

| | |
|---|---|
| Negative Response | 43 |
| Positive Response | 49 |
| No Data | 9 |

```
SEQ ID NO:1 - Rv3879c
MSITRPTGSYARQMLDPGGWVEADEDTFYDRAQEYSQVLQRVTDVLDTCR

QQKGHVFEGGLWSGGAANAANGALGANINQLMTLQDYLATVITWHRHIAG

LIEQAKSDIGNNVDGAQREIDILENDPSLDADERHTAINSLVTATHGANV

SLVAETAERVLESKNWKPPKNALEDLLQQKSPPPPDVPTLVVPSPGTPGT

PGTPITPGTPITPGTPITPIPGAPVTPITPTGTPVTPVTPGKPVTPVTP

VKPGTPGEPTPITPVTPPVAPATPATPATPVTPAPAPHPQPAPAPAPSPG

PQPVTPATPGPSGPATPGTPGGEPAPHVKPAALAEQPGVPGQHAGGGTQS

GPAHADESAASVTPAAASGVPGARAAAAAPSGTAVGAGARSSVGTAAASG

AGSHAATGRAPVATSDKAAAPSTRAASARTAPPARPPSTDHIDKPDRSES

ADDGTPVSMIPVSAARAARDAATAAASARQRGRGDALRLARRIAAALNAS

DNNAGDYGFFWITAVTTDGSIVVANSYGLAYIPDGMELPNKVYLASADHA

IPVDEIARCATYPVLAVQAWAAFHDMTLRAVIGTAEQLASSDPGVAKIVL

EPDDIPESGKMTGRSRLEVVDPSAAAQLADTTDQRLLDLLPPAPVDVNPP

GDERHMLWFELMKIPMTSTATGREAAHLRAFRAYAAHSQEIALHQAHTAT

DAAVQRVAVADWLYWQYVTGLLDRALAAAC
```

SEQ ID NO's 2 to 18-Rv3879c peptides mentioned in Table 2

```
POOL 1
 2 MSITR PTGSY ARQML

3 PTGSY ARQML DPGGW

4 ARQML DPGGW VEADE

5 DPGGW VEADE DTFYD

6 VEADE DTFYD RAQEY

7 DTFYD RAQEY SQVLQ

POOL 2
 8 RAQEY SQVLQ RVTDV

9 SQVLQ RVTDV LDTCR

10 RVTDV LDTCR QQKGH

11 LDTCR QQKGH VFEGG

12 QQKGH VFEGG LWSGG

13 VFEGG LWSGG AANAA

POOL 3
14 LWSGG AANAA NGALG

15 AANAA NGALG ANINQ

16 NGALG ANINQ LMTLQ

17 ANINQ LMTLQ DYLAT

18 LMTLQ DYLAT VITWH

ESAT-6
MTEQQWNFAGIEAAASAIQGNVTSIHSLLDEGKQSLTKLAAAWGGSGSEA

YQGVQQKWDATATELNNALQNLARTISEAGQAMASTEGNVTGMFA

CFP10
MAEMKTDAATLAQEAGNFERISGDLKTQIDQVESTAGSLQGQWRGAAGTA

AQAAVVRFQEAANKQKQELDEISTNIRQAGVQYSRADEEQQQALSSQMGF
```

The invention claimed is:

1. A method of increasing the sensitivity of a diagnostic test for diagnosing

*Mycobacterium tuberculosis* infection in a human, wherein said diagnostic test comprises contacting T cells from said human with a *Mycobacterium tuberculosis* antigen which is not Rv3879c, and determining whether any of the said T-cells recognise said antigen; said method additionally comprising (i) contacting T-cells from said human with one or more of (a) a peptide consisting of the sequence of SEQ ID NO: 1;

(b) a peptide consisting of the sequence of at least 8 consecutive amino acids of the sequence shown in SEQ ID NO: 1; or (c) a peptide consisting of a sequence which is capable of binding to a T-cell receptor which recognises a peptide as defined in (a) or (b); and (ii) determining whether any of the said T-cells recognise said peptide, wherein the method is optionally carried out in vitro.

2. A method according to claim 1, wherein step (i) further comprises contacting said T-cells with one or more further *Mycobacterium tuberculosis* T-cell antigen(s) or with an analogue(s) of said antigen(s) which is capable of binding to a T-cell receptor which recognises said antigen(s).

3. A method according to claim 2, wherein said one or more further *Mycobacterium tuberculosis* antigens include antigens encoded by the RD-1 or RD-2 region, which antigens are preferably ESAT-6 and/or CFP10; or fragments thereof which are at least 8 amino acids long.

4. A method according to claim 1, wherein said *Mycobacterium tuberculosis* antigen which is not Rv3879c is selected from Rv3873, Rv3878 or Rv1989c; or fragments thereof which are at least 8 amino acids long.

5. A method according to claim 1, wherein step (i) comprises contacting said sample of T-cells with two or more different peptides, each consisting of the sequence of at least 8 consecutive amino acids of the sequence shown in SEQ ID NO: 1.

6. A method according to claim 1 wherein peptides from, or analogues of, at least five different antigens are contacted with the T cells.

7. A method according to claim 1 wherein one or more of the peptides (i) consisting of any one of SEQ ID NO's 2 to 18, or (ii) which bind to a T-cell which recognise (i), are contacted with the T cells.

8. A method according to claim 1, wherein recognition of said peptide by said T-cells is determined by detecting the secretion of a cytokine from the T-cells.

9. A method according to claim 1, wherein the cytokine is IFN-γ.

10. A method according to claim 8, wherein said cytokine is detected by allowing said cytokine to bind to an immobilised antibody specific to said cytokine and detecting the presence of the antibody/cytokine complex.

11. A method according to claim 1, wherein said T-cells are freshly isolated ex vivo cells.

12. A method according to claim 1, wherein said T-cells have been cultured in vitro.

13. A diagnostic composition comprising a peptide as defined in step (a), (b) or (c) of claim 1 and one or more further *Mycobacterium tuberculosis* T-cell antigens selected from (i) Rv3873 and Rv1989c or a fragment thereof which is at least 8 amino acids long, or (ii) an analogue of (i) which binds to a T-cell which recognises (i).

14. A composition according to claim 13 further comprising one or more *Mycobacterium tuberculosis* antigens are selected from (i) ESAT-6, CFP10, and Rv3878, or fragment of any thereof which is at least 8 amino acids long; or (ii) an analogue of (i) which binds to a T-cell which recognises (i).

15. A kit for diagnosing *Mycobacterium tuberculosis* infection or exposure in a human, comprising a composition as defined in claim 13, and optionally a means for detecting recognition of a peptide by T-cells.

16. A kit according to claim 15, wherein said means for detecting recognition of a peptide by T-cells comprises an antibody to a cytokine.

17. A kit according to claim 16, wherein said antibody is immobilised on a solid support and wherein said kit optionally comprises a means to detect an antibody/cytokine complex.

18. A kit according to claim 16, wherein said cytokine is IFN-γ.

19. A method of ascertaining the stage of a *Mycobacterium tuberculosis* infection in a human comprising determining whether there is a differential T cell response to different *Mycobacterium tuberculosis* antigens in the human, comprising:

(i) determining the T-cell response to at least one of Rv3879c, Rv3873, Rv3878, and Rv1989c;

(ii) determining the T-cell response to ESAT-6 and CFP-10; and (iii) comparing the responses in (i) and (ii); wherein, where the T-cell response is positive to at least one of the antigens of step (i) and negative to the antigens of step (ii), the stage of the infection is deemed to be recent.

* * * * *

SEQUENCE LISTING

<160> NUMBER OF SEQ ID NOS: 33

<210> SEQ ID NO 1
<211> LENGTH: 729
<212> TYPE: PRT
<213> ORGANISM: Mycobacterium tuberculosis

<400> SEQUENCE: 1

```
Met Ser Ile Thr Arg Pro Thr Gly Ser Tyr Ala Arg Gln Met Leu Asp
1               5                   10                  15

Pro Gly Gly Trp Val Glu Ala Asp Glu Asp Thr Phe Tyr Asp Arg Ala
            20                  25                  30

Gln Glu Tyr Ser Gln Val Leu Gln Arg Val Thr Asp Val Leu Asp Thr
        35                  40                  45

Cys Arg Gln Gln Lys Gly His Val Phe Glu Gly Gly Leu Trp Ser Gly
    50                  55                  60

Gly Ala Ala Asn Ala Ala Asn Gly Ala Leu Gly Ala Asn Ile Asn Gln
65                  70                  75                  80

Leu Met Thr Leu Gln Asp Tyr Leu Ala Thr Val Ile Thr Trp His Arg
                85                  90                  95

His Ile Ala Gly Leu Ile Glu Gln Ala Lys Ser Asp Ile Gly Asn Asn
            100                 105                 110

Val Asp Gly Ala Gln Arg Glu Ile Asp Ile Leu Glu Asn Asp Pro Ser
        115                 120                 125

Leu Asp Ala Asp Glu Arg His Thr Ala Ile Asn Ser Leu Val Thr Ala
    130                 135                 140

Thr His Gly Ala Asn Val Ser Leu Val Ala Glu Thr Ala Glu Arg Val
145                 150                 155                 160

Leu Glu Ser Lys Asn Trp Lys Pro Lys Asn Ala Leu Glu Asp Leu
                165                 170                 175

Leu Gln Gln Lys Ser Pro Pro Pro Asp Val Pro Thr Leu Val Val
            180                 185                 190

Pro Ser Pro Gly Thr Pro Thr Pro Thr Pro Ile Thr Pro Gly
    195                 200                 205

Thr Pro Ile Thr Pro Gly Thr Pro Ile Thr Pro Ile Pro Gly Ala Pro
    210                 215                 220

Val Thr Pro Ile Thr Pro Thr Pro Gly Thr Pro Val Thr Pro Val Thr
225                 230                 235                 240

Pro Gly Lys Pro Val Thr Pro Val Thr Pro Val Lys Pro Gly Thr Pro
                245                 250                 255

Gly Glu Pro Thr Pro Ile Thr Pro Val Thr Pro Val Ala Pro Ala
            260                 265                 270

Thr Pro Ala Thr Pro Ala Thr Pro Val Thr Pro Ala Pro Ala Pro His
    275                 280                 285

Pro Gln Pro Ala Pro Ala Pro Ala Pro Ser Pro Gly Pro Gln Pro Val
    290                 295                 300

Thr Pro Ala Thr Pro Gly Pro Ser Gly Pro Ala Thr Pro Gly Thr Pro
305                 310                 315                 320

Gly Gly Glu Pro Ala Pro His Val Lys Pro Ala Ala Leu Ala Glu Gln
                325                 330                 335

Pro Gly Val Pro Gly Gln His Ala Gly Gly Thr Gln Ser Gly Pro
            340                 345                 350

Ala His Ala Asp Glu Ser Ala Ala Ser Val Thr Pro Ala Ala Ala Ser
        355                 360                 365
```

Gly Val Pro Gly Ala Arg Ala Ala Ala Ala Pro Ser Gly Thr Ala
            370                 375                 380

Val Gly Ala Gly Ala Arg Ser Ser Val Gly Thr Ala Ala Ser Gly
385                 390                 395                 400

Ala Gly Ser His Ala Ala Thr Gly Arg Ala Pro Val Ala Thr Ser Asp
                405                 410                 415

Lys Ala Ala Pro Ser Thr Arg Ala Ser Ala Arg Thr Ala Pro
                420                 425                 430

Pro Ala Arg Pro Pro Ser Thr Asp His Ile Asp Lys Pro Asp Arg Ser
            435                 440                 445

Glu Ser Ala Asp Asp Gly Thr Pro Val Ser Met Ile Pro Val Ser Ala
    450                 455                 460

Ala Arg Ala Ala Arg Asp Ala Ala Thr Ala Ala Ala Ser Ala Arg Gln
465                 470                 475                 480

Arg Gly Arg Gly Asp Ala Leu Arg Leu Ala Arg Ile Ala Ala Ala
                485                 490                 495

Leu Asn Ala Ser Asp Asn Asn Ala Gly Asp Tyr Gly Phe Phe Trp Ile
                500                 505                 510

Thr Ala Val Thr Thr Asp Gly Ser Ile Val Val Ala Asn Ser Tyr Gly
            515                 520                 525

Leu Ala Tyr Ile Pro Asp Gly Met Glu Leu Pro Asn Lys Val Tyr Leu
    530                 535                 540

Ala Ser Ala Asp His Ala Ile Pro Val Asp Glu Ile Ala Arg Cys Ala
545                 550                 555                 560

Thr Tyr Pro Val Leu Ala Val Gln Ala Trp Ala Ala Phe His Asp Met
                565                 570                 575

Thr Leu Arg Ala Val Ile Gly Thr Ala Glu Gln Leu Ala Ser Ser Asp
            580                 585                 590

Pro Gly Val Ala Lys Ile Val Leu Glu Pro Asp Asp Ile Pro Glu Ser
    595                 600                 605

Gly Lys Met Thr Gly Arg Ser Arg Leu Glu Val Asp Pro Ser Ala
            610                 615                 620

Ala Ala Gln Leu Ala Asp Thr Thr Asp Gln Arg Leu Leu Asp Leu Leu
625                 630                 635                 640

Pro Pro Ala Pro Val Asp Val Asn Pro Pro Gly Asp Glu Arg His Met
                645                 650                 655

Leu Trp Phe Glu Leu Met Lys Pro Met Thr Ser Thr Ala Thr Gly Arg
                660                 665                 670

Glu Ala Ala His Leu Arg Ala Phe Arg Ala Tyr Ala Ala His Ser Gln
            675                 680                 685

Glu Ile Ala Leu His Gln Ala His Thr Ala Asp Ala Ala Val Gln
    690                 695                 700

Arg Val Ala Val Ala Asp Trp Leu Tyr Trp Gln Tyr Val Thr Gly Leu
705                 710                 715                 720

Leu Asp Arg Ala Leu Ala Ala Ala Cys
                725

<210> SEQ ID NO 2
<211> LENGTH: 15
<212> TYPE: PRT
<213> ORGANISM: Mycobacterium tuberculosis -continued

```
<400> SEQUENCE: 2

Met Ser Ile Thr Arg Pro Thr Gly Ser Tyr Ala Arg Gln Met Leu
1               5                   10                  15

<210> SEQ ID NO 3
<211> LENGTH: 15
<212> TYPE: PRT
<213> ORGANISM: Mycobacterium tuberculosis

<400> SEQUENCE: 3

Pro Thr Gly Ser Tyr Ala Arg Gln Met Leu Asp Pro Gly Gly Trp
1               5                   10                  15

<210> SEQ ID NO 4
<211> LENGTH: 15
<212> TYPE: PRT
<213> ORGANISM: Mycobacterium tuberculosis

<400> SEQUENCE: 4

Ala Arg Gln Met Leu Asp Pro Gly Gly Trp Val Glu Ala Asp Glu
1               5                   10                  15

<210> SEQ ID NO 5
<211> LENGTH: 15
<212> TYPE: PRT
<213> ORGANISM: Mycobacterium tuberculosis

<400> SEQUENCE: 5

Asp Pro Gly Gly Trp Val Glu Ala Asp Glu Asp Thr Phe Tyr Asp
1               5                   10                  15

<210> SEQ ID NO 6
<211> LENGTH: 15
<212> TYPE: PRT
<213> ORGANISM: Mycobacterium tuberculosis

<400> SEQUENCE: 6

Val Glu Ala Asp Glu Asp Thr Phe Tyr Asp Arg Ala Gln Glu Tyr
1               5                   10                  15

<210> SEQ ID NO 7
<211> LENGTH: 15
<212> TYPE: PRT
<213> ORGANISM: Mycobacterium tuberculosis

<400> SEQUENCE: 7

Asp Thr Phe Tyr Asp Arg Ala Gln Glu Tyr Ser Gln Val Leu Gln
1               5                   10                  15

<210> SEQ ID NO 8
<211> LENGTH: 15
<212> TYPE: PRT
<213> ORGANISM: Mycobacterium tuberculosis

<400> SEQUENCE: 8

Arg Ala Gln Glu Tyr Ser Gln Val Leu Gln Arg Val Thr Asp Val
1               5                   10                  15

<210> SEQ ID NO 9
<211> LENGTH: 15
<212> TYPE: PRT
<213> ORGANISM: Mycobacterium tuberculosis
```

-continued

```
<400> SEQUENCE: 9

Ser Gln Val Leu Gln Arg Val Thr Asp Val Leu Asp Thr Cys Arg
1               5                   10                  15

<210> SEQ ID NO 10
<211> LENGTH: 15
<212> TYPE: PRT
<213> ORGANISM: Mycobacterium tuberculosis

<400> SEQUENCE: 10

Arg Val Thr Asp Val Leu Asp Thr Cys Arg Gln Gln Lys Gly His
1               5                   10                  15

<210> SEQ ID NO 11
<211> LENGTH: 15
<212> TYPE: PRT
<213> ORGANISM: Mycobacterium tuberculosis

<400> SEQUENCE: 11

Leu Asp Thr Cys Arg Gln Gln Lys Gly His Val Phe Glu Gly Gly
1               5                   10                  15

<210> SEQ ID NO 12
<211> LENGTH: 15
<212> TYPE: PRT
<213> ORGANISM: Mycobacterium tuberculosis

<400> SEQUENCE: 12

Gln Gln Lys Gly His Val Phe Glu Gly Gly Leu Trp Ser Gly Gly
1               5                   10                  15

<210> SEQ ID NO 13
<211> LENGTH: 15
<212> TYPE: PRT
<213> ORGANISM: Mycobacterium tuberculosis

<400> SEQUENCE: 13

Val Phe Glu Gly Gly Leu Trp Ser Gly Gly Ala Ala Asn Ala Ala
1               5                   10                  15

<210> SEQ ID NO 14
<211> LENGTH: 15
<212> TYPE: PRT
<213> ORGANISM: Mycobacterium tuberculosis

<400> SEQUENCE: 14

Leu Trp Ser Gly Gly Ala Ala Asn Ala Ala Asn Gly Ala Leu Gly
1               5                   10                  15

<210> SEQ ID NO 15
<211> LENGTH: 15
<212> TYPE: PRT
<213> ORGANISM: Mycobacterium tuberculosis

<400> SEQUENCE: 15

Ala Ala Asn Ala Ala Asn Gly Ala Leu Gly Ala Asn Ile Asn Gln
1               5                   10                  15

<210> SEQ ID NO 16
<211> LENGTH: 15
<212> TYPE: PRT
<213> ORGANISM: Mycobacterium tuberculosis
```

-continued

<400> SEQUENCE: 16

Asn Gly Ala Leu Gly Ala Asn Ile Asn Gln Leu Met Thr Leu Gln
1               5                   10                  15

<210> SEQ ID NO 17
<211> LENGTH: 15
<212> TYPE: PRT
<213> ORGANISM: Mycobacterium tuberculosis

<400> SEQUENCE: 17

Ala Asn Ile Asn Gln Leu Met Thr Leu Gln Asp Tyr Leu Ala Thr
1               5                   10                  15

<210> SEQ ID NO 18
<211> LENGTH: 15
<212> TYPE: PRT
<213> ORGANISM: Mycobacterium tuberculosis

<400> SEQUENCE: 18

Leu Met Thr Leu Gln Asp Tyr Leu Ala Thr Val Ile Thr Trp His
1               5                   10                  15

<210> SEQ ID NO 19
<211> LENGTH: 95
<212> TYPE: PRT
<213> ORGANISM: Mycobacterium tuberculosis

<400> SEQUENCE: 19

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
            35                  40                  45

Glu Ala Tyr Gln Gly Val Gln Gln Lys Trp Asp Ala Thr Ala Thr Glu
        50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 20
<211> LENGTH: 100
<212> TYPE: PRT
<213> ORGANISM: Mycobacterium tuberculosis

<400> SEQUENCE: 20

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Ala Leu Ser Ser
                85                  90                  95

Gln Met Gly Phe
            100

<210> SEQ ID NO 21
<211> LENGTH: 15
<212> TYPE: PRT
<213> ORGANISM: Mycobacterium tuberculosis

<400> SEQUENCE: 21

Leu Thr Ala Thr Asn Phe Phe Gly Ile Asn Thr Ile Pro Ile Ala
1               5                   10                  15

<210> SEQ ID NO 22
<211> LENGTH: 15
<212> TYPE: PRT
<213> ORGANISM: Mycobacterium tuberculosis

<400> SEQUENCE: 22

Tyr Phe Ile Arg Met Trp Asn Gln Ala Ala Leu Ala Met Glu Val
1               5                   10                  15

<210> SEQ ID NO 23
<211> LENGTH: 15
<212> TYPE: PRT
<213> ORGANISM: Mycobacterium tuberculosis

<400> SEQUENCE: 23

Leu Asp Pro Gly Ala Ser Gln Ser Thr Thr Asn Pro Ile Phe Gly
1               5                   10                  15

<210> SEQ ID NO 24
<211> LENGTH: 15
<212> TYPE: PRT
<213> ORGANISM: Mycobacterium tuberculosis

<400> SEQUENCE: 24

Ala Ala Lys Leu Ala Gly Leu Val Phe Pro Gln Pro Pro Ala Pro
1               5                   10                  15

<210> SEQ ID NO 25
<211> LENGTH: 15
<212> TYPE: PRT
<213> ORGANISM: Mycobacterium tuberculosis

<400> SEQUENCE: 25

Glu Ser Leu Val Ser Asp Gly Leu Pro Gly Val Lys Ala Ala Leu
1               5                   10                  15

<210> SEQ ID NO 26
<211> LENGTH: 15
<212> TYPE: PRT
<213> ORGANISM: Mycobacterium tuberculosis

<400> SEQUENCE: 26

Leu Val Ala Thr Asn Phe Phe Gly Ile Asn Thr Ile Pro Ile Ala
1               5                   10                  15

<210> SEQ ID NO 27
<211> LENGTH: 15
<212> TYPE: PRT
<213> ORGANISM: Mycobacterium tuberculosis

```
<400> SEQUENCE: 27

Leu Met Ala Thr Asn Phe Phe Gly Ile Asn Thr Ile Pro Ile Ala
1               5                   10                  15

<210> SEQ ID NO 28
<211> LENGTH: 15
<212> TYPE: PRT
<213> ORGANISM: Mycobacterium tuberculosis

<400> SEQUENCE: 28

Met Val Ala Thr Asn Phe Phe Gly Ile Asn Thr Ile Pro Ile Ala
1               5                   10                  15

<210> SEQ ID NO 29
<211> LENGTH: 15
<212> TYPE: PRT
<213> ORGANISM: Mycobacterium tuberculosis

<400> SEQUENCE: 29

His Tyr Gly Glu Met Trp Ala Gln Asp Ala Leu Ala Met Tyr Gly
1               5                   10                  15

<210> SEQ ID NO 30
<211> LENGTH: 15
<212> TYPE: PRT
<213> ORGANISM: Mycobacterium tuberculosis

<400> SEQUENCE: 30

Asp Tyr Val Arg Met Trp Leu Gln Ala Ala Ala Val Met Gly Leu
1               5                   10                  15

<210> SEQ ID NO 31
<211> LENGTH: 15
<212> TYPE: PRT
<213> ORGANISM: Mycobacterium tuberculosis

<400> SEQUENCE: 31

Gln Tyr Ala Glu Met Trp Ser Gln Asp Ala Met Ala Met Tyr Gly
1               5                   10                  15

<210> SEQ ID NO 32
<211> LENGTH: 61
<212> TYPE: PRT
<213> ORGANISM: Mycobacterium tuberculosis

<400> SEQUENCE: 32

Met Ala Thr Thr Pro Ser Leu Pro Glu Ile Ala Ala Asn His Ile Thr
1               5                   10                  15

Gln Ala Val Leu Thr Ala Thr Asn Phe Phe Gly Ile Asn Thr Ile Pro
                20                  25                  30

Ile Ala Leu Thr Glu Met Asp Tyr Phe Ile Arg Met Trp Asn Gln Ala
        35                  40                  45

Ala Leu Ala Met Glu Val Tyr Gln Ala Glu Thr Ala Val
    50                  55                  60

<210> SEQ ID NO 33
<211> LENGTH: 52
<212> TYPE: PRT
<213> ORGANISM: Mycobacterium tuberculosis
```

-continued

```
<400> SEQUENCE: 33

Ala Met Val Pro Pro Pro Val Val Ala Ala Asn Arg Ala Gln His Met
1               5                   10                  15

Ser Leu Val Ala Thr Asn Phe Phe Gly Gln Asn Thr Pro Ala Ile Ala
            20                  25                  30

Ala Thr Glu Ala Gln Tyr Glu Glu Met Trp Ala Gln Asp Ala Ala Ala
        35                  40                  45

Met Tyr Gly Tyr
    50
```